United States Patent [19]

Walker et al.

[11] 4,450,877
[45] May 29, 1984

[54] PHARMACEUTICAL PREPARATIONS IN SOLID UNIT DOSAGE FORM

[75] Inventors: Stephen E. Walker, Buckingham; Keith Bedford, Newport Pagnell; Terence Eaves, Woburn Sands, all of England

[73] Assignee: Hoechst Aktiengesellschaft, Frankfurt am Main, Fed. Rep. of Germany

[21] Appl. No.: 416,046

[22] Filed: Sep. 8, 1982

Related U.S. Application Data

[63] Continuation of Ser. No. 210,219, Nov. 25, 1980, which is a continuation of Ser. No. 956,448, Nov. 1, 1978, abandoned.

[30] Foreign Application Priority Data

Nov. 3, 1977 [GB] United Kingdom .............. 45755/77

[51] Int. Cl.³ ................................................ B65B 3/04
[52] U.S. Cl. .......................................... 141/1; 264/4; 424/78
[58] Field of Search ..................... 141/129–198, 141/250–284, 1–12, 37–96; 424/78, 81; 264/4; 53/266 R

[56] References Cited

U.S. PATENT DOCUMENTS

| | | | |
|---|---|---|---|
| 1,378,536 | 5/1921 | Flynn | 331/126.7 A |
| 2,987,082 | 6/1961 | Schaub | 141/141 |
| 3,807,464 | 4/1974 | Pitesky | 141/258 |
| 3,903,939 | 9/1975 | Pickett | 141/198 |
| 3,927,196 | 12/1975 | Hersh | 424/37 |
| 3,935,885 | 2/1976 | Alter | 141/141 |

FOREIGN PATENT DOCUMENTS

| | | |
|---|---|---|
| 1933562 | 1/1971 | Fed. Rep. of Germany . |
| 1617362 | 3/1971 | Fed. Rep. of Germany . |
| 2157201 | 5/1973 | Fed. Rep. of Germany . |
| 2340010 | 3/1974 | Fed. Rep. of Germany . |
| 2301664 | 8/1974 | Fed. Rep. of Germany . |
| 2357503 | 5/1975 | Fed. Rep. of Germany . |
| 2546371 | 4/1977 | Fed. Rep. of Germany . |
| 2546577 | 4/1977 | Fed. Rep. of Germany . |
| 1380009 | 1/1975 | United Kingdom . |
| 1427881 | 3/1976 | United Kingdom . |
| 1442951 | 7/1976 | United Kingdom . |
| 1560406 | 2/1980 | United Kingdom . |

OTHER PUBLICATIONS

Journal of Pharmaceutical Sciences 64, pp. 320–322 (1975).

Primary Examiner—Houston S. Bell, Jr.
Attorney, Agent, or Firm—Curtis, Morris & Safford

[57] ABSTRACT

A process for the manufacture of pharmaceutical preparations in hard capsule form and a capsule filling machine equipped with a detector system and a filling head suitable for dosing a liquid.

12 Claims, 3 Drawing Figures

PHARMACEUTICAL PREPARATIONS IN SOLID UNIT DOSAGE FORM

This is a continuation of application Ser. No. 210,219 filed Nov. 25, 1980 which is a continuation of parent application Ser. No. 956,448 filed Nov. 1, 1978, now abandoned.

The invention relates to the manufacture of pharmaceutical preparations in hard capsule form, preferably in hard gelatin capsule form.

It is important that pharmaceutical preparations should contain a known amount of active ingredient, and in many cases precise dosing is required, especially in the case of highly potent drugs to be administered in small quantities. For oral administration, solid unit dosage forms are generally preferred to liquid forms because they permit precise doses to be administered, they are generally more convenient to administer, and they are often more stable. Hard gelatin capsules are a relatively expensive but highly acceptable solid unit dosage form, the gelatin shells generally being filled with solid material. However, the processing of solids into granules and powders for filling into capsules presents certain technical problems, for example, the difficulty of providing a uniform dispersion of the active ingredient in the carriers used.

A capsule-filling machine has recently been described (DOS No. 26 12 472) whereby paste-like or semi-solid materials can be dosed into hard gelatin capsule shells. The paste-like or semi-solid material is extruded into a layer of uniform thickness and density, and a tubular member is inserted vertically through the whole thickness of the layer. As a result of the pasty consistency of the material to be dosed, a plug of the material is retained with the member and is then forced out from the member into a capsule shell and located by means of compressed air. This system has several disadvantages: the accuracy of the dosing depends on producing a layer of extruded material of very uniform thickness and must overcome the difficulties of mixing the drug in the pasty base; the tubular member must be controlled by a relatively complex mechanism which twists the member from its position over the extruded layer to its position over the capsule shell; it is difficult to discharge the plug of material from the member; and if an oily material is used, this may tend to leak from the joint of the capsule.

The use of liquid material in capsules presents problems as the liquid tends to leak out from between the halves of the capsule shell. This leakage can be avoided by placing a band around the joint: however, this adds an extra stage to the filling process, thus adding to the manufacturing costs. Liquids may, however, be used in soft gelatin capsules. Soft gelatin capsules combine the advantage of a solid unit dosage form with the advantages of a liquid with regard to the ease of providing a uniform mix of the active ingredient in the carrier and the precision with which the resulting mix can be dispensed. However, they have the disadvantage that very specialised equipment is required for their production which is therefore generally carried out by contract manufacturers rather than by the pharmaceutical house itself. This results in a higher cost than for hard gelantin capsules and also has other disadvantages, for example, problems associated with research and development of new pharmaceuticals.

Not only should the amount of active ingredient in a pharmaceutical preparation be known, but also the extent and rate of its release in vivo, that is to say, its bioavailability. Work has been done to formulate preparations having a high bioavailability of the active ingredient, and, in many cases, specific release properties. Work has been proceeding since the 1960's in the use of solid solutions, solid dispersions and eutectic mixtures consisting of the active ingredient in a suitable carrier, for example urea or a polyethylene glycol. It has been shown (see for example *Journal of Pharmaceutical Sciences* 60 1281 (1971)) that such systems using hydrophilic carriers, for example polyethylene glycols, can result in a bioavailability much superior to conventional solid formulations, while hydrophobic carriers may be used to delay the release of the active principle. Suitable hydrophobic matrices include, for example, low melting-point waxes, oils, and water-insoluble polymers. In the latter case, the water-insoluble polymer may be present in admixture with a liquid hydrophilic carrier: slow-release soft gelatin capsules have been described in which the liquid core comprises polyethylene glycol 600 and a few percent of polyvinyl acetate; as the PEG is dissolved by the gastric juices, the water present causes the polyvinyl actate to precipitate as a solid, thus slowing the release of the active ingredient. As the proportion of polyvinyl acetate present increases, the rate of release of the active ingredient decreases.

The disadvantage, however, of the large scale use of solid dispersions or eutectic mixtures is that they generally have very poor processing properties, generally being sticky, glass-like masses with poor flow properties, which are very difficult to process using conventional tablet-making or capsule-filling techniques.

The present invention provides a process for the manufacture of a pharmaceutical preparation in unit dosage form, which comprises dosing into a rigid shell suitable for administration as a dosage unit, preferably into a hard gelatin capsule, a liquid carrier containing the active ingredient, which liquid solidifies or gels sufficiently to lose its liquid flow properties, inside the shell, the liquid carrier being a water-soluble hot melt having a solidification point in the range of 30° to 60° C. or being a thixotropic gel.

The shell is suitably the body of a hard gelatin capsule.

The liquid carrier containing the active ingredient may be, for example, a thixotropic gel which behaves as a liquid during the filling operation but which behaves as a solid inside the capsule shell, or it may be a water soluble hot melt which will solidify on cooling to room temperature to give a solid solution, a solid dispersion of a eutectic mixture, or a mixture of these forms: for example, a drug may partially dissolve in a molten carrier so that on solidification a mixture of a solid solution and a solid dispersion results. Generally, in a solid dispersion, the drug is present as individual crystals and not as crystal aggregates as in conventional formulations, thereby aiding dissolution.

When using a hot melt, it is desirable to use a system having a melting point in the range from 30° to 60° C. and a relatively low viscosity when molten. This ensures that the melt can be readily pumped through the capsule filling system and can easily be stirred when molten, to aid dissolution and the suspension of any insoluble material. The upper temperature which may be used is determined by the upper temperature which may be used is determined by the stability of the active ingredient in the molten carrier, the case and economy of heating the capsule-filling machinery, and the stability of the capsule shells: a temperature in excess of 60° C. may cause damage to a conventional hard gelatin capsule shell, but a higher temperature may be used when other hard capsules are filled.

Water-soluble carriers which may be used are for example: macrogol esters as polyoxyl-40-stearate, macrogol ethers as polyethylene glycols, poloxamer as poloxamer 188, polyvinyl alcohols sucrose esters, for example crodesta F 160, carboxypolymethylene as carbopol, sorbitan esters as sorbitan trioleate, poysorbates as polysorbate 80 or any mixture thereof.

By suitable choice of the carrier material, the in vivo dissolution of the drug may be enhanced and the bioavailability of the drug may be increased. In a solid solution or dispersion or a eutectic mixture, the drug is present in a much more finely divided form than can be obtained by simply mixing the drug with a solid carrier. If the carrier or the solid solution, dispersion or eutectic mixture is very readily soluble in gastric juices, it will dissolve very rapidly on administration and the drug, being in very finely divided form, will be easily and rapidly absorbed. This is a great advantage for drugs which are not very readily soluble in gastric juices. Polyethylene glycols (PEG) having molecular weights in the range from 1000 to 6000 have proved to be suitable carriers for such fast release systems; the melting point of the system can be finely controlled by mixing various grades of PEG, for example PEG 1000 having a melting point of about 35° C. and PEG 6000 having a melting point of about 60° C.

On the other hand, if the carrier is not readily soluble in gastric juices, a slow-release system will be obtained; such carriers include oils, for example liquid paraffin, gelled with thixotropic agents. An effective slow-release formulation can also be produced using polyvinyl acetate as described above, in admixture, however, with a higher grade of PEG than has been used in soft gelatin capsules, so as to produce a solid solution in the capsule.

Suitable gelling agents which are available for the production of thixotropic gels include hydrogenated castor oil, (for example ®Thixcin), and colloidal silicon dioxide (for example ®Aerosil).

Because the process of the invention utilises a liquid carrier, the problems associated with obtaining a uniform mix of a solid drug with a solid carrier are not encountered. A homogeneous mixture or solution can be obtained simply by stirring the hot melt or liquid gel. This is especially important for systems where it is difficult to mix solids efficiently: for example, certain low-dose oral contraceptives have a particle size and shape which makes it very difficult to produce solid unit dosage forms having satisfactory content uniformity. It has been described that, for example, the content of steroids in low dosage contracentive tablets varies within rather wide limits (c.f. Paper presented by P. D. Faint and G. H. King at Technicon Colloquim on "Automated Analysis in the Pharmaceutical Industry", Bloomsbury Centre Hotel, London, Apr. 23rd, 1970). Such steroids are therefore very suitably filled into capsule shells using the process of the invention. The process of the invention may also, for example, be used for the preparation of capsules containing Digoxin, in the dissolution problems of which there has been much recent interest.

A great advantage of the process of the invention is that the capsules can be filled using conventional hard gelatin capsule filling machinery with some modification. Such machinery for filling powders into a capsule shell has a filling head which picks up a plug of powder and drops the plug into a capsule shell located on a turnable which subsequently rotates to bring a new shell into position or filling. The machinery can be readily modified to carry out the process of the invention by replacing the filling head with means for dosing a liquid rather than a powder.

The invention relates therefore furthermore to a capsule filling machine comprising a turntable and a filling head, characterized in that the machine is equipped with a detector system and a filling head suitable for dosing a liquid. As filling head there may be used for example a refillable syringe, a peristaltic pump or a precision shot dispenser. Of these, a precision shot dispenser operated by compressed air has proved especially suitable, providing an accurate and repeatable dose of liquid.

If a hot melt is used, heating means is required to ensure that the melt does not solidify or become unduly viscous before it is dosed into the capsule shell: the temperature of the melt when dosed into the body of the capsule shell should of course be lower than the temperature at which damage will be caused to the shell. Heating tape around the relevant parts of the apparatus is generally the most convenient heating means, but other methods, for example hot air, may also be used.

In a conventional hard gelatin capsule filling machine, a receptable is generally provided beneath the filling station so that, if the machine fails to prevent a capsule body to the filling head, the discharged material is collected. However, when the machine is modified to dispense a liquid, this collection system is inadequate as the liquid soils the apparatus. This can be avoided by incorporating a detector system, for example based on a photo-cell, so that no liquid is discharged from the filling mechanism unless a capsule shell is correctly positioned under the filling mechanism. This system is preferably extended to detect and prevent the filling of damaged shells. The detector system may for example actuate a micro-switch which controls the turntable and the filling mechanism; preferably, if a capsule shell is not presented to the filling mechanism, no liquid is dispensed and the turntable rotates to present the next capsule shell so that the filling cycle is not seriously disrupted.

The capsule filling machine may be of the intermittent motion type or of the continuous motion type.

Capsules may be prepared which contain incompatible drugs, by dosing the shell with a liquid containing one drug and, after solidification, dosing the shell with a liquid containing a second drug. Similarly, capsules dosed with a melt and/or gel may also contain pellets, granules, tablets or a powder.

Thus by the process of the invention there are obtained the advantages of a liquid with regard to the content uniformity of the resulting product, and the advantages of a solid with regard to convenience of administration and stability of the preparation. In addition, there may be obtained the advantages of the use of solid solutions, solid dispersions and eutectic mixtures with regard to the control of release of the drug and its bioavailability. A further significant advantage is that a formulation used in the process of the invention is generally very much simpler than that required using conventional tableting or capsule-filling techniques, which generally require the presence of various carriers acting as flow aids, lubricants, and diluents to improve the flow properties of the formulation. In the process of the invention, the liquid formulation is of course self-lubricating and may have a very simple constitution, for example a polyethylene glycol and the drug, or an oil, a thixotropic agent and the drug.

The invention will now be described, by way of example only, with reference to the accompanying drawings, in which.

Figure 1:
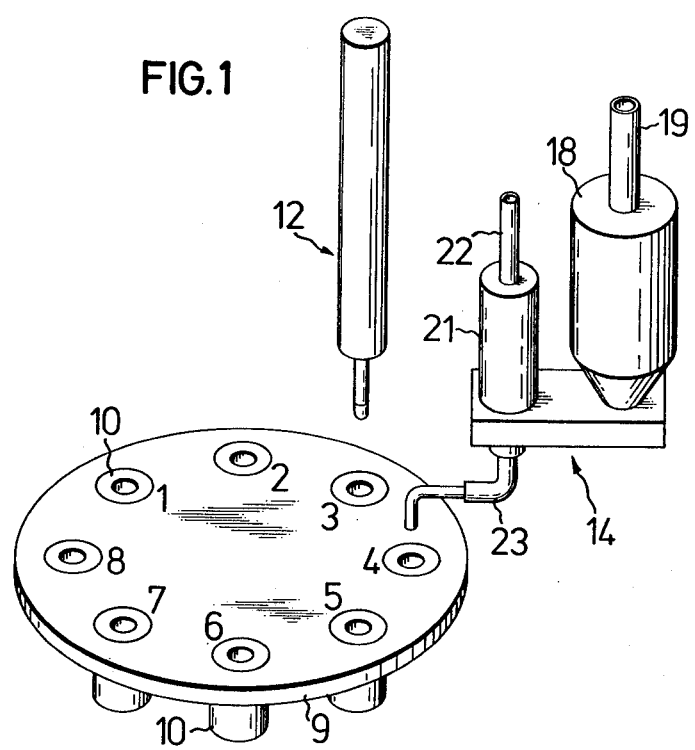
FIG. 1 shows the turntable of a capsule-filling machine of the invention and its associated filling equipment.

FIG. 1 shows the turntable 9 of the capsule filling machine which has eight stations arranged around its periphery. These stations are the capsule introducing station 1, separation station 2, detection station 3, filling station 4, capsule closing station 5, ejection station 6, control station 7 and a station 8 which is not used in the process of the invention.

At capsule introduction station 1, an empty capsule shell is placed into a capsule holder 10 on the turntable 9. At separation station 2 the capsule cap is separated from the capsule body 11. Over detection station 3 there is positioned a detector system 12. At filling station 4, liquid filling material 13 is injected into the capsule body 11 by means of a precision shot dispenser 14. At station 5 the capsule shell is closed by replacing the cap on the capsule body 11 and the resulting capsule is ejected from the turntable at ejection station 6. The actuator (a microswitch, not shown) for the precision shot dispenser 14 activated by the turntable 9 is located at control station 7.

Figures 2, 3:
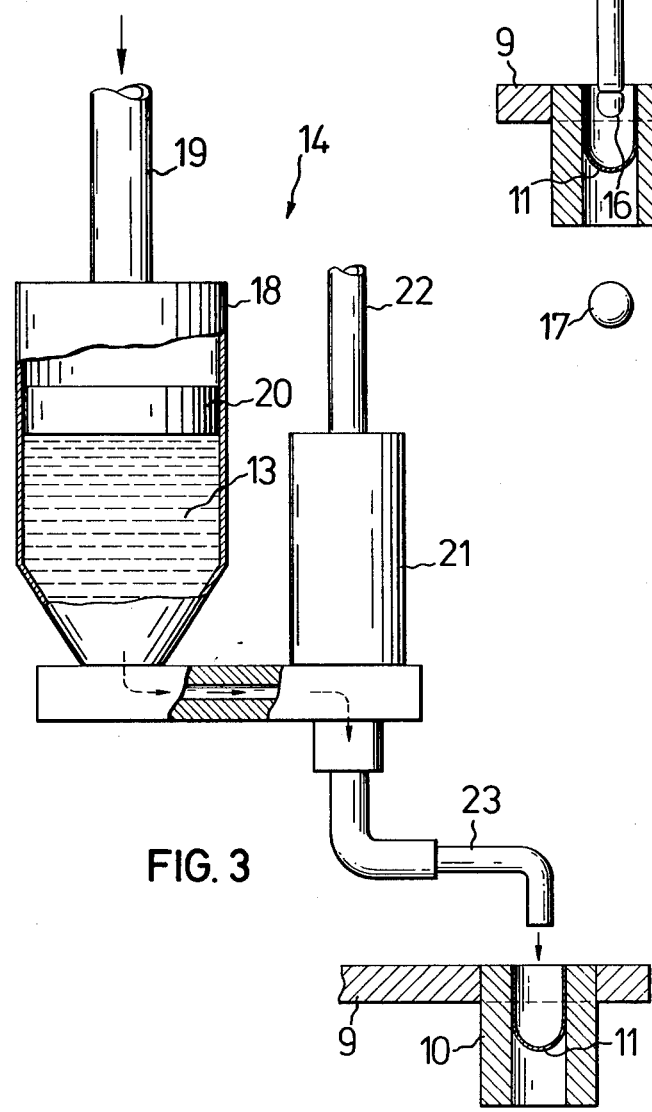
FIG. 2 shows the capsule detection system of the machine of FIG. 1.
FIG. 3 shows the precision shot dispenser used in the machine of FIG. 1.

The detector system 12 is shown more clearly in FIG. 2. It comprises a support bar 15 which is movable in a vertical plane by means not shown, a light emitting diode 16 and a detector 17. If the capsule body 11 is not present in the capsule holder 10, light from the light emitting diode 16 reaches the detector 17 hereby actuating the microswitch (not shown) at control station 7 which delays the filling cycle, thus preventing spillage of the liquid filling material 13.

The precision shot dispenser 14 is shown in FIG. 3. It comprises a reservoir 18 for the liquid filling material 13 having an inlet for compressed air which operates a plunger 20; a valve mechanism 21 wherein the valve is opened or closed by means of compressed air introduced through an inlet 22 permits the flow of liquid filling material 13 in the direction of the arrows into a filling nozzle 23 and subsequently into the capsule body 11. The reservoir 18 is provided with heating means (not shown), for example heating tape or a hot-air blower. The quantity of liquid filling material 13 dispensed depends on the pressure of the air applied at inlet 19 and on a timer device (not shown) which is controlled by the microswitch (not shown) at control station 7. It also depends on such parameters as the viscosity of the liquid filling material 13.

For carrying out the process of the invention the precision shot dispenser may be modified, for example, the plunger 20 may be omitted.

The following Examples illustrate the invention.

EXAMPLE 1

| Formula | mg/capsule |
|---|---|
| Triamterene | 0.020 |
| Polyethylene glycol (400) | 80.000 |
| Polyethylene glycol (2000) | 320.000 |
| TOTAL FILL WEIGHT | 400.020 mg |

A conventional Zanasi capsule filling machine was modified for use by replacement of the normal means for dosing a plug of powder into the capsule shell by a refillable syringe. A hot air blower was provided to keep the filling mechanism at the required temperature, and a detector system utilising a light emitting diode was fitted so that if for any reason a capsule shell was not presented at the correct time to the refillable syringe, the filling cycle was stopped. A Hoflinger capsule filling machine may be similarly modified.

The polyethylene glycol mixture was melted at 50° C. and the Triamterene was dispersed therein by stirring. 3,600 capsules (size 1) were filled per hour with the melt, and the relative standard deviation (RSD) of the fill weight was 2.7%. By comparison, a run of 3,600 capsules per hour dosed with a mean fill weight of 269.23 mg of a conventional powder formulation based on microcrystalline cellulose, diluents, magnesium stearate and talc, showed a relative standard deviation of 2.9%. Fill weight uniformity is therefore shown to be similar to that achieved by conventional equipment. Content uniformity of the drug in the capsule has also been determined and even with a low dose of 20 μg Triamterene the relative standard deviation of the drug in the mix is less than 2%. This compares favourably with the content variation shown by low dose contraceptive steroids prepared by conventional tableting methods.

EXAMPLE 2

| Formula | mg/capsule |
|---|---|
| Colloidal silicon dioxide (for ex.(R)AEROSIL 200) | 12.4 |
| hydrogenated castor oil (for ex.(R)THIXCIN R) | 18.6 |
| Liquid paraffin | 589.0 |
| TOTAL FILL WEIGHT | 620 mg |

Thixcin and Aerosil are dispersed in the liquid paraffin using a high speed mixer and the mix is warmed to 40° C. to develop the gel. The thixotropic gel is filled into capsule shells using a precision-shot dispenser. For a fill weight of 620 mg a relative standard deviation of 1.4% can be achieved.

EXAMPLE 3

| Formula | mg/capsule |
|---|---|
| Triamterene | 50 |
| Polyethylene glycol (400) | 70 |
| Polyethylene glycol (2000) | 280 |
| TOTAL FILL WEIGHT | 400 mg |

Method

Triamterene is dispersed in the Polyethylene glycol 400 using a triple roller mill, molten PEG 2000 is added with stirring. The molten mix is filled into capsules using a refillable syringe.

The dissolution in 900 ml of 0.1 N HCl by the United States Pharmacopoeia method at 100 rpm, of capsules of Triamterene filled by the process of the invention and commercially available Triamterene are shown in the table:

| Dissolution of Triamterene 50 mg capsules-USP method 900 ml 0.1 N HCl at 100 rmp | | |
|---|---|---|
| | % drug released Dose | |
| | 50 mg Dose Form | 50 mg |
| | Commercially available Triamterene capsules | Solid Solution (example 3) |
| Dissolution Time (Mins) | | |
| 15 | 2 | 78 |
| 30 | 6 | 97 |
| 60 | 13 | 99 |
| 240 | 46 | — |
| 360 | 60 | — |
| Disintegration Time BP (Mins) | 30 | 9* |

*the capsule contents disperse very quickly and the major part of this time is taken by the capsule shell dissolving.

EXAMPLE 4

| Formula | mg/capsule |
|---|---|
| Nomifensine Hydrogen Maleate | 75 |
| Polyvinyl acetate | 10-30 (2-6% w/v) |
| Polyethylene glycol | 415-395 |
| TOTAL FILL WEIGHT | 500 mg |

METHOD

The P.E.G. mixture is melted at 50° C. and the Polyvinyl acetate is dissolved in the molten mass with stirring. Nomifensine hydrogen maleat dispersed in the melt and the whole is filled into capsule shells using a refillable syringe. Such formulations have a slow release action: as water contacts the polyvinylacetate, precipitation occurs thus slowing the release of the drug.

Dissolution data are shown in the Table:

| Desaga flow through dissolution test of Nomifensine 75 mg Retard; influence of polyvinylacetate concentration | | | |
|---|---|---|---|
| PVA Concn % | % drug released | | |
| Time (hours) | 2 | 4 | 6 |
| 1.25 | 83 | 53 | 43 |
| 2.25 | 84 | 61 | 47 |
| 3.25 | 84 | 65.2 | 48 |
| 4.25 | — | 70.0 | 49 |
| 5.25 | — | 74.5 | 50 |

The effect of polyvinylacetate content of the retard formulation is illustrated in the above Table. A graded response is seen;

2%—high release in the first time period and no retard action

4%—satisfactory initial release and gradual retard release for the remaining four hours.

6%—satisfactory initial release with little further drug release over the remaining four hours.

What is claimed is:

1. A process for the manufacture of a pharmaceutical preparation in unit dosage form, which comprises the steps of preparing a liquid carrier containing an active ingredient and a liquid which solidifies or gels sufficiently to lose its liquid flow properties said liquid carrier being a thixotropic gelling agent, and dosing said liquid carrier containing the active ingredient in its liquid form into a rigid shell suitable for administration as a dosage unit.

2. The process of claim 1, wherein the liquid carrier comprises a polyethylene glycol having a molecular weight in the range of from 1000 to 6000, a mixture of two or more such polyethylene glycols or a mixture of one or more such polyethyleneglycols with polyvinyl acetate.

3. The process of claim 1, wherein the thixotropic gelling agent is hydrogenated castor oil or colloidal silicon dioxide.

4. The process of claim 1, wherein the rigid shell is the body of a hard gelatin capsule.

5. The process of claim 1, wherein the dosing takes place in a high-speed hard gelatin capsule filling machine.

6. The process defined in claim 1 wherein the liquid carrier containing the active ingredient is dosed into the rigid shell using a capsule filling machine which is equipped with a detector system and a filling head suitable for dosing a liquid.

7. The process defined in claim 1 wherein the liquid carrier containing the active ingredient is dosed into the rigid shell using a capsule filling machine which is equipped with a detector system and a refillable syringe, a peristaltic pump or a precision shot dispenser as filling head.

8. The process defined in claim 1 which comprises detecting the presence or absence of a shell to receive a dosage unit before dosing the shell with liquid carrier and active ingredient.

9. A process for the manufacture of a pharmaceutical preparation in unit dosage form, which comprises the steps of dispersing an active ingredient into a liquid carrier which is a thixotropic gelling agent and maintained in its liquid form, dosing said liquid carrier containing the active ingredient into a rigid shell suitable for administration as a dosage unit, and thereafter permitting said carrier in said shell to solidify.

10. The process of claim 18, wherein the liquid carrier comprises a polyethylene glycol having a molecular weight in the range of from 1000 to 6000, a mixture of two or more such polyethylene glycols or a mixture of one or more such polyethyleneglycols with polyvinyl acetate.

11. The process of claim 18, wherein the thixotropic gelling agent is hydrogenated castor oil or colloidal silicon dioxide.

12. A pharmaceutical preparation in unit dosage form manufactured by the process defined by claim 1.

* * * * *

UNITED STATES PATENT AND TRADEMARK OFFICE
CERTIFICATE OF CORRECTION

PATENT NO. : 4,450,877
DATED : May 29, 1984
INVENTOR(S) : Walter et al.

It is certified that error appears in the above-identified patent and that said Letters Patent is hereby corrected as shown below:

Claim 10, line 1, change "18" --9--.

Claim 11, line 1, change "18" to --9--.

Signed and Sealed this

Fourteenth Day of May 1985

[SEAL]

Attest:

DONALD J. QUIGG

Attesting Officer

Acting Commissioner of Patents and Trademarks